United States Patent
Stahl et al.

(10) Patent No.: US 10,440,982 B2
(45) Date of Patent: Oct. 15, 2019

(54) CEREAL-BASED INFANT NUTRITION WITH FIBRE

(71) Applicant: N.V. NUTRICIA, Zoetermeer (NL)

(72) Inventors: Bernd Stahl, Rosbach-Rodheim (DE); Martine Sandra Alles, Apeldoorn (NL); Brigitte Antonia Maria Borgmann, Oberursel (DE)

(73) Assignee: N. V. NUTRICIA, Zoetermeer (NL)

( * ) Notice: Subject to any disclaimer, the term of this patent is extended or adjusted under 35 U.S.C. 154(b) by 166 days.

(21) Appl. No.: 15/168,369

(22) Filed: May 31, 2016

(65) Prior Publication Data

US 2017/0027216 A1 Feb. 2, 2017

Related U.S. Application Data

(60) Division of application No. 13/914,009, filed on Jun. 10, 2013, now abandoned, which is a division of application No. 12/532,583, filed on Mar. 26, 2010, now abandoned, which is a continuation-in-part of application No. PCT/NL2008/115062, filed on Mar. 21, 2008.

(30) Foreign Application Priority Data

Mar. 22, 2007 (NL) .................. PCT/NL2007/050121

(51) Int. Cl.
*A23L 33/21* (2016.01)
*A23L 33/00* (2016.01)
*A23L 7/10* (2016.01)

(52) U.S. Cl.
CPC .............. *A23L 33/21* (2016.08); *A23L 7/198* (2016.08); *A23L 33/40* (2016.08); *A23V 2002/00* (2013.01); *A23V 2250/5116* (2013.01)

(58) Field of Classification Search
CPC ........... A23L 33/21; A23L 33/40; A23L 7/198
USPC ....................................................... 514/54
See application file for complete search history.

(56) References Cited

U.S. PATENT DOCUMENTS

| | | | |
|---|---|---|---|
| 5,260,279 A | 11/1993 | Greenberg | |
| 5,472,952 A | 12/1995 | Smidt et al. | |
| 6,489,310 B1 | 12/2002 | Brassart et al. | |
| 6,890,571 B2 | 5/2005 | Shi et al. | |
| 2003/0118712 A1 | 6/2003 | Navarro Y Koren et al. | |
| 2005/0084592 A1* | 4/2005 | Aldred ................. | A23L 29/206 426/573 |

FOREIGN PATENT DOCUMENTS

| EP | 1634599 A1 | 3/2006 |
|---|---|---|
| EP | 1714660 A1 | 10/2006 |

OTHER PUBLICATIONS

Englyst et al. Classification and measurement of nutritionally important starch fractions. European Journal of Clinical Nutrition 46 (Suppl. 2):S33-S50, 1992. (Year: 1992).*
Bosscher et al. Availabilities of Calcium, Iron, and Zinc From Dairy Infant Formulas Is Affected by Soluble Dietary Fibers and Modified Starch Fractions. Nutrition 19:641-645, 2003. (Year: 2003).*
S. Fanaro et al., Acidic Oligosaccharides From Pectin Hydrolysate as New Component for Infant Formulae: Effect on Intestinal Flora, Stool Characteristics and PH, Jour Pediatric Gastroenterol. Nutr., Aug. 2005, 41:186-90.
Moore, N., Chao, C., Yang, L.-P., Storm, H., Oliva-Hemker, M., Saavedra, J.M. (2003) Effects of fructo-oligosaccharidesupplemented infant cereal: a double-blind, randomized trial. British Journal of Nutrition, vol. 90, p. 581-587.
Mondal, S.K., Sen Gupta, P.G., Gupta, D.N., Ghosh, S., Sikder, S.N., Rajendran, K., Saha, M.R., Sircar, B.K., Bhattacharya,S.K. (1996) Ocurrence of diarrhoeal diseases in relation to infant feeding practices in rural community in West Bengal, IndiaActa Paediatrica, vol. 85, p. 1159-1162.
Ramakrishna, B.S., Venkataraman, S., Srinivasan, P., Dash, P., Young, G.P., Binder, H.J. (2000) Amylase-Resistant Starch Plus Oral Rehydration Solution for Cholera. The New England Journal of Medicine, vol. 342, No. 5, p. 308-313.
Commission Directive 96/8/EC of on foods intended for use in energy-restricted diets for weight reduction (Text with EEA relevance) Feb. 26, 1996 (OJ L 55, Jun. 3, 1996, p. 22).
EFSA Journal 2014;12(7):3760 Suggested citation: EFSA NDA Panel (EFSA Panel on Dietetic Products, Nutrition and Allergies), 2014. Scientific Opinion on the essential composition of infant and follow-on formulae. EFSA Journal 2014:12(7):3760, 106 pp.

* cited by examiner

*Primary Examiner* — Yih-Horng Shiao
(74) *Attorney, Agent, or Firm* — Browdy and Neimark, PLLC

(57) ABSTRACT

Cereal-based semi-liquid and/or semi-solid compositions suitable for supporting the transition period wherein the infant changes from a diet consisting of breast milk or liquid infant formula to solid adult foods, comprising uronic acid carbohydrates with a degree of polymerization (DP) between 10 and 300 and also uses thereof are disclosed.

15 Claims, 1 Drawing Sheet

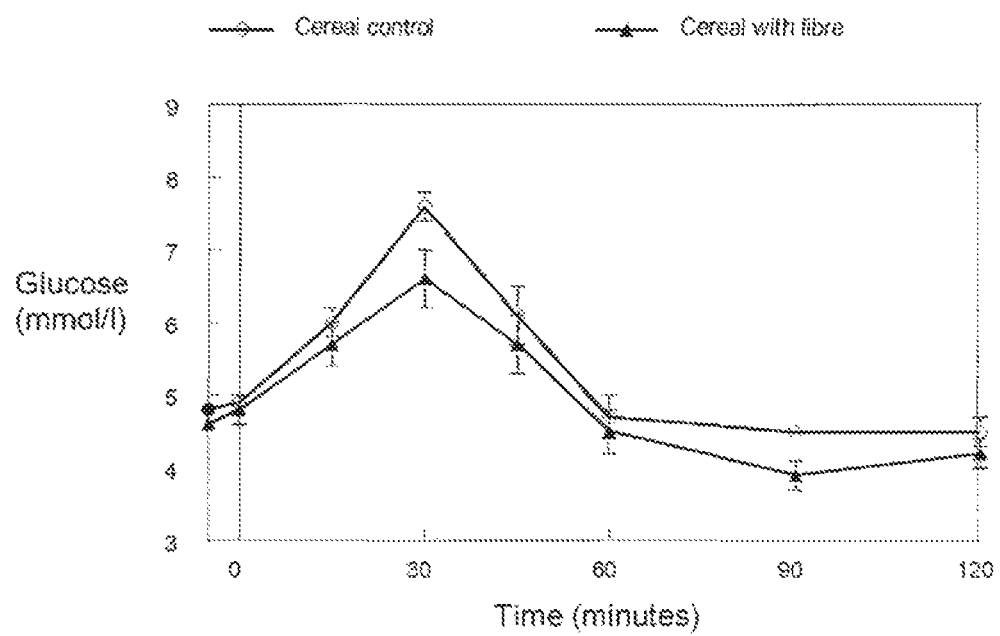

CEREAL-BASED INFANT NUTRITION WITH FIBRE

FIELD OF THE INVENTION

The present invention relates to the field of spoonable cereal-based infant nutrition.

BACKGROUND OF THE INVENTION

Fibres are of significant importance for a healthy nutrition. Some fibres have been described to improve bowel habit, intestinal flora, and gut barrier and prevent diarrhoea or intestinal infections. Furthermore, oral intake of fibres increases satiety and blunts blood glucose fluctuations.

Infants exclusively receiving breast milk consume fibres in the form of soluble, non-digestible oligosaccharides. Breast milk comprises, on average, about 10 g neutral oligosaccharides per liter and 1 g acidic oligosaccharides per liter.

The adult diet includes a mixture of fibres, comprising soluble non-starch polysaccharides (including uronic acid carbohydrates), insoluble non-starch polysaccharides, non-digestible oligosaccharides, and resistant starch. The recommended fibre intake for an adult is about 30 g per day.

Upon the transition to solid food, an infant changes from a diet exclusively consisting of breast milk or liquid infant formula to a more mature diet. It is extremely important that the fibre component present in the adult nutrition is gradually introduced into the infant's diet. In this way the microflora and the colonic food is changed gradually, and gastrointestinal discomfort, such as bloating, abdominal pain, flatulence, diarrhoea and constipation is avoided. Furthermore, during the transition from liquid to solid food, semi-liquid and/or semi-solid foods are preferred. These foods are preferably consumed with a spoon.

"Milchbrei Apfel Karote" from Milupa (Germany) is a dry powder cereal product. After reconstitution with water, a spoonable cereal-based infant nutrition is formed comprising rice- and maize flour and apple and carrot powder.

SUMMARY OF THE INVENTION

The present invention provides a semi-liquid and/or semi-solid cereal-based nutrition that is particularly suitable for supporting the transition period wherein the infant changes from a diet exclusively consisting of breast milk or liquid infant formula to mature, solid nutrition. The present composition is particularly designed to have the infant accustomed to fibre ingredients present in the adult diet.

The cereal nutrition is of a semi-liquid and/or semi-solid constitution, with a viscosity of between 150 and 100,000 mPas. By providing nutrition with this viscosity an intermediate between liquid and solid food is provided. This enables the infant to get accustomed to eating in contrast to drinking only and enables the acquaintance with eating with a spoon. Solid food is still inappropriate for infants changing from breast milk or infant (liquid) formula, because of the infant's lack of teeth and its poor swallowing reflex.

The present nutritional composition is adapted to meet the requirements of infants in the transition phase by providing a combination of a cereal component, an intermediate concentration of fibres and uronic acid carbohydrates with a degree of polymerisation (DP) of 10 to 300 monosaccharide units. A DP of 10 to 300 monosaccharide units is also herein referred to as medium, medium DP or medium chain carbohydrate. This DP is intermediate between the major acidic oligosaccharides found in human breast milk having a DP below 10, and the native, high DP pectin as found in the mature human nutrition, e.g. in the cell walls of vegetables and fruits, generally having a DP above 300. The present uronic acid carbohydrate with an intermediate DP has intermediate effects regarding the anti-pathogenic and bifidogenic effects of human milk acidic oligosaccharides and the blood glucose and satiety regulating effects of native pectin.

Furthermore, medium DP pectin has advantageous product-technological properties, such as reduction of viscosity increasing effects and/or reduction of undesirable texturising effects, i.e. an unwanted mouthfeel effect compared to native pectin. This enables the inclusion of intermediate length uronic acid molecules in cereal products without a dramatic increase in viscosity. This is of utmost importance because these products usually already have a high viscosity and a further increase could result in an undesirable product. Particularly, minimal or negligible increase in viscosity by addition of medium chain uronic acid molecules is remarkable since normally pectin forms rigid gels when combined with (calcium comprising) milk products.

By administering the present cereal-based nutritional composition, gastrointestinal discomfort, such as bloating, abdominal pain, flatulence, diarrhoea and constipation is avoided. At the same time, the present composition provides the advantages of fibres available in breast milk (such as anti-pathogenic and bifidogenic effects) and the advantages of fibres present in the adult diet (such as blood glucose and satiety regulating effects). It was found by the inventors that the cereal based nutrition of the present invention comprising a relatively small amount of fibre, attenuated blood glucose levels, despite the presence of a high concentration of glucose containing digestible carbohydrates.

DETAILED DESCRIPTION OF PREFERRED EMBODIMENTS

The present invention provides a nutritional composition with a viscosity at 20° C. and at a shear rate of 10 s$^{-1}$ between 150 and 100,000 mPas, comprising: 10 to 99 wt. % cereal component based on dry weight of the nutritional composition, 1.0 to 30 wt. % fibre based on dry weight of the nutritional composition, and 0.5 to 100 wt. % uronic acid carbohydrate with a degree of polymerisation of 10 to 300 based on total fibre.

In a further aspect the present invention provides a method for providing nutrition to an infant, said method comprising administering said nutritional composition to the infant.

In still a further aspect the present invention provides a method for regulation of blood glucose, decreasing postprandial blood glucose levels, and/or prolonging the release of energy, said method comprising administering the present nutritional composition.

In still a further aspect the present invention provides a method for regulation of blood glucose, decreasing postprandial blood glucose levels, and/or prolonging the release of energy, said method comprising administering the present fibre mixture comprising uronic acid carbohydrate with a degree of polymerisation of 10 to 300, inulin, resistant starch and oat fibre.

In another aspect the present invention provides a method for increasing satiety and/or improving sleep, said method comprising administering the present nutritional composition.

In still a further aspect the present invention provides a method for increasing satiety and/or improving sleep, said method comprising administering the present fibre mixture comprising uronic acid carbohydrate with a degree of polymerisation of 10 to 300, inulin, resistant starch and oat fibre.

In yet a further aspect, the present invention provides a method for treating and/or preventing constipation, diarrhoea and/or gastro-intestinal infections said method comprising administering the present nutritional composition.

The present invention also provides a process for the manufacture of a nutritional composition, comprising admixing a powder comprising: 10 to 99 wt. % cereal component based on dry weight of the powder, 1 to 30 wt. % fibre based on total dry weight of the powder, and 0.5 to 100 wt. % uronic acid carbohydrate with a degree of polymerisation of 10 to 300 based on total fibre and a liquid.

The present invention also provides a powder composition comprising: 10 to 99 wt. % cereal flour, ground cereal and/or milled cereal based on dry weight of the powder composition, 1.0 to 30 wt. % fibre based on dry weight of the powder composition, and 0.5 to 100 wt. % uronic acid carbohydrate with a degree of polymerisation of 10 to 300 based on total fibre. A more preferred embodiment is a powder composition comprising 20 to 90 wt. % cereal flour and/or milled cereals and/or ground cereals based on dry weight of the powder composition, 1.5 to 20 wt. % fibre based on dry weight of the powder composition, 0.5 to 86 wt. % uronic acid carbohydrate with a degree of polymerisation of 10 to 300 based on total fibre, 10 to 95 wt. % inulin based on total fibre, 2 to 80 wt. % resistant starch based on total fibre, and 2 to 80 wt. % oat fibre based on total fibre, the remaining of the powder being comprised of other components such as milk powder and/or powdered infant formula. In one aspect the present invention also concerns a nutritional composition comprising a fibre mixture comprising 0.5 to 86 wt. % uronic acid carbohydrate with a degree of polymerisation of 10 to 300 based on total fibre, 10 to 95 wt. % inulin based on total fibre, 2 to 80 wt. % resistant starch based on total fibre, and 2 to 80 wt. % oat fibre based on total fibre.

In a further aspect the present invention provides a method for regulation of blood glucose, decreasing postprandial blood glucose levels, and/or prolonging the release of energy, said method comprising administering the present fibre mixture comprising 0.5 to 86 wt. % uronic acid carbohydrate with a degree of polymerisation of 10 to 300 based on total fibre, 10 to 95 wt. % inulin based on total fibre, 2 to 80 wt. % resistant starch based on total fibre, and 2 to 80 wt. % oat fibre based on total fibre.

In still a further aspect the present invention provides a method for increasing satiety and/or improving sleep, said method comprising administering the present fibre mixture comprising 0.5 to 86 wt. % uronic acid carbohydrate with a degree of polymerisation of 10 to 300 based on total fibre, 10 to 95 wt. % inulin based on total fibre, 2 to 80 wt. % resistant starch based on total fibre, and 2 to 80 wt. % oat fibre based on total fibre.

Cereal

The present composition comprises a cereal component. Cereal components are an important part of the infant's diet, and are usually one of the first non-breast milk and non-infant formulae components introduced into the diet of infants. Ultimately, the infant will consume a high cereal diet, including bread, rice and pasta.

The present cereal component preferably is a component selected from the group consisting of whole cereal, cereal flour, milled cereal, ground cereals, cereal starch, and cereal fibre. The present cereal component is preferably a component selected from the group consisting of cereal flour, ground cereal and milled cereal. The cereal flour preferably comprises cereal flour which is dextrinised by heat treatment and/or cereal flour which has been enzyme treated in order to degrade the cereal starch. Preferably, the present composition comprises a precooked cereal component, more preferably precooked cereal flour. The term "precooked cereal flour" indicates flour obtained by the process whereby flour, in granular and crystalline structure is swelled and transformed, preferably in a continuous amorphous phase, in the presence of heat and water, dried (e.g. using drum drying or extrusion cooking) and ground. The precooked flour presently used preferably comprises between 5 and 15 wt. % protein based on the total dry weight of the precooked flour. The use of precooked flour has the further advantage that the final product has a reduced content of thermo-resistant spores compared to the use of non-precooked flour. Furthermore, the use of precooked flour in the present process has the advantage that the viscosity of the composition is more stable after reconstitution of the product with a warm liquid. This is in contrast to the situation wherein solely non-precooked flour is used. In the latter case the viscosity gradually increases with time.

The precooked flour used in the present invention preferably has a degree of gelatinisation of at least 50%, preferably at least 75%. This gives better water holding capacity (WHC), resulting in an improved product (e.g. stability and palatability). The WHC of the precooked material used in the present invention is preferably between 2 and 10 g water/g dry matter precooked material, more preferably between 2.5 and 5 g water/g dry matter precooked material. The WHC can be determined as described by Pinnavaia and Pizzirani (Starch/Starke 50 (1998) nr. 2-3, S. 64-67).

Preferably the present composition comprises at least one cereal selected from the group consisting of rice, millet, sorghum, wheat, barley, buckwheat, maize (corn), fonio, oats, quinoa, rye, triticale, teff, wild rice, spelt, amaranth, quinoa and starchy root crops. Starchy root crops are preferably selected from the group consisting of potato, sweet potato, cassava, yams, aroids, oca, ulluco and mashua. Preferably, the present composition is gluten free. The intake of gluten by infants below 6 month of age can result in gastro-intestinal damage. Hence, the present composition preferably comprises one or more cereal components selected from the group consisting of rice, maize and millet, sorghum, teff, oat and starchy root crops. More preferably, the present composition comprises one or more cereal components selected from the group consisting of rice, maize and millet, teff, and oat. More preferably the cereal component of the present composition consists of rice, maize and millet, sorghum, teff, oat, starchy root crops and mixtures thereof. More preferably the present cereal is selected from the group consisting of rice, maize, oat, teff and millet. Preferably the cereal part of the composition comprises mixtures of cereal components. Typically the cereal is processed as defined in EU directive 96/5/EC.

The present composition preferably comprises between 10 and 99 g cereal component per 100 g dry weight of the present composition, more preferably between 20 and 90 g, even more preferably between 25 and 80 g.

Fibre Components

The term "fibre" as used in the present invention typically relates to all soluble non-digestible carbohydrates (SNC), insoluble non-starch polysaccharides (INSP), resistant starch and lignin. The present uronic acid carbohydrate is also a fibre. Uronic acid carbohydrates belong to the class of SNC. The term "non-digestible" as used in the present invention refers to carbohydrates which are not digested in the intestine by the action of acids or digestive enzymes present in the human upper digestive tract (small intestine and stomach) and reach the colon. Sugars such as lactose and sucrose are considered digestible. The term "soluble" as used herein, when having reference to a carbohydrate, polysaccharide, fibre or oligosaccharide, means that the substance is at least 50% soluble according to the method described by L. Prosky et al., *J. Assoc. Off Anal. Chem.* 71:1017-1023 (1988). The term "insoluble" as used herein, when having reference to a carbohydrate, polysaccharide, fibre or oligosaccharide, means that the substance is less than 50% soluble according to the method described by L. Prosky et al., *J. Assoc. Off Anal. Chem.* 71:1017-1023 (1988). For instance, an oat fibre being composed of 60 wt. % insoluble fibre and 40 wt. % soluble fibre is classified as insoluble fibre.

The present nutritional composition comprises 1 to 30 wt. % fibre based on dry weight of the total composition, preferably 1.5 to 20 wt. %, more preferably 2 to 10 wt %. Preferably one serving of the present composition comprises 0.5 to 5 g fibre, more preferably 1 to 3 g fibre.

Uronic Acid Carbohydrates

Uronic acid carbohydrates are soluble, non-starch poly- and oligosaccharides. The term uronic acid carbohydrate as used in the present invention refers to a carbohydrate wherein at least 50% of the residues are selected from the group consisting of guluronic acid, mannuronic acid, galacturonic acid, glucuronic acid, riburonic, iduronic, N-acetylneuramic acid and neuramic acid. The term galacturonic acid carbohydrate as used in the present invention refers to a carbohydrate wherein at least 50% of the residues are galacturonic acid residues.

The present nutritional composition preferably comprises 0.5 to 100 wt. % uronic acid carbohydrates with a DP of 10 to 300 based on total fibre, preferably at least 1 wt. %, more preferably at least 2 wt. %, even more preferably at least 5 wt. %. In a preferred embodiment, the composition comprises, of 0.01 to 30 wt. % uronic acid carbohydrate with a DP of 10 to 300 based on dry weight of the present composition, more preferably 0.05 to 10 wt. %, even more preferably 0.1 to 5 wt. %. More preferably, the present nutritional composition comprises 0.5 to 100 wt. % uronic acid carbohydrates with a DP of 20 to 200 based on total fibre, preferably at least 1 wt. %, more preferably at least 2 wt. %, even more preferably at least 5 wt. %. In a more preferred embodiment, the composition comprises of 0.01 to 30 wt. % uronic acid carbohydrate with a DP of 20 to 200 based on dry weight of the present composition, more preferably 0.05 to 10 wt. %, even more preferably 0.1 to 5 wt. %.

The present composition comprises preferably between 50 and 100 wt. % uronic acid carbohydrate with a DP of 10 to 300 based on total weight of uronic acid carbohydrates in the present composition, more preferably 75 to 100 wt. %. A sufficient amount of medium chain (DP of 10 to 300) uronic acid carbohydrates compared to short (DP<10) and long (DP>300) carbohydrates ensures a proper transition to full length uronic acid molecules present in the mature diet.

In a preferred embodiment the uronic acid carbohydrate comprises at least 50% galacturonic acid residues based on total uronic acid residues in the uronic acid carbohydrate. Preferably, the present composition comprises 25 to 100 wt. % galacturonic acid carbohydrates with a DP of 10 to 300, more preferably 20 to 300, based on total weight of uronic acid carbohydrates in the present composition. In a preferred embodiment, the uronic acid carbohydrates of the present invention comprises between 50 and 100 wt. % galacturonic carbohydrates with a DP of 10 to 300, more preferably 20 to 200, based on total weight of uronic acid carbohydrates. Hence, preferably the present invention comprises at least 50 to 100 wt. % pectin molecules with a DP between 10 and 300, more preferably 20 to 200, based on total weight of uronic acid. Pectin frequently occurs in the adults diet, and hence advantageously medium chain (DP of 10 to 300) pectin is used in the present composition.

The present composition preferably comprises less than 25 wt. % of the uronic acid carbohydrates with a DP above 300, more preferably above 200, based on total weight of uronic acid carbohydrates. The present composition preferably comprises less than 25 wt. % uronic acid carbohydrates with a DP below 10, more preferably below 20, based on total weight of uronic acid carbohydrates. By including the uronic acid carbohydrate with a DP of 10 to 300, more preferably of 20 to 300, both physiological effects of acidic oligosaccharides found with a DP below 10 in breast milk and native pectins with an average DP above 300 ranging up to over 30000 are provided, which is advantageous for infants changing from breast milk or from infant formulae to adult food.

In a preferred embodiment, at least one of the terminal hexose units of the uronic acid carbohydrate has a double bond, which is preferably situated between the $C_4$ and $C_5$ position of the terminal hexose unit.

The double bond effectively protects against attachment of the pathogenic bacteria against the epithelium. Preferably one of the terminal hexose units comprises the double bond. The double bond at terminal hexose unit can for example be obtained by enzymatically degrading pectin with lyase. Preferably at least 5%, more preferably at least 10%, even more preferably at least 25% of the terminal hexose units of the uronic acid carbohydrate is an unsaturated hexose unit. As each individual uronic acid carbohydrate preferably comprises only one unsaturated terminal hexose unit, preferably less than 50%, more preferably less than 40% of the terminal hexose comprises a double bond.

The uronic acid carbohydrate may be esterified, such as acetylated, methylated, methoxylated and/or amidated. In one embodiment the uronic acid carbohydrates are preferably characterised by a degree of esterification, preferably methoxylation, below 70%, preferably below 50%, more preferably below 30%. A low degree of esterification advantageously results in easier fermentation by the intestinal flora and/or an increased anti-adhesive effect on pathogenic bacteria.

In one embodiment the uronic acid carbohydrates have a degree of esterification, preferably methoxylation above 20%, preferably above 50% even more preferably above 60%. Preferably the uronic acid carbohydrates have a degree of methylation above 10%, preferably above 20%, preferably above 50% even more preferably above 70%. A high degree of esterification advantageously increases the bioavailability of cations, preferably calcium, iron and/or magnesium.

Preferably, the present uronic acid carbohydrate has a viscosity of below 50 mPas, preferably below 30 mPas at a 2 wt. % solution in water at 25° C. and a shear rate of $10 \text{ s}^{-1}$.

Suitable methods to obtain medium DP uronic acid carbohydrates are described in Van Deventer-Schriemik & Pilnik, 1987, Acta Alimentaria 16:143-153. A preferred source of uronic acid carbohydrates is partially degraded alginate or partially degraded pectin from citrus fruits, apples, and/or sugar beet, more preferably partially degraded pectin from apple. A preferred source of the present uronic acid carbohydrate is modified citrus pectin. Modified citrus pectin is preferably obtained by lysis to smaller molecular weight molecules by treatment at pH 10 and at a pH of 3 for a longer period of time. Modified citrus pectin is comprised of linear polygalacturonate chains comprising from 5 to 90 galacturonic acid residues, with an average of approximately 55 residues. Modified citrus pectin is also known as modified pectin, depolymerised pectin and pH-modified pectin. Another preferred source of uronic acid carbohydrate is ultra low viscosity pectin which is partially degraded, such as Herbapekt SF 50 LV (Herbafood) or ultralow viscosity pectin from Obipektin.

Soluble Non-Digestible Carbohydrates

The present composition preferably further comprises soluble, non-digestible carbohydrates other than uronic acid carbohydrates (hereinafter abbreviated to SNC). Preferably the present composition comprises a soluble non-digestible carbohydrate selected from the group consisting of galacto-oligo- and/or polysaccharide (including transgalacto-oligo- and/or polysaccharides), xylo-oligo- and/or polysaccharide, gluco-oligo- and/or polysaccharide (including gentio-oligosaccharides, malto-oligosaccharides, isomalto-oligosaccharides, resistant dextrins and cyclodextrins), arabino-oligo- and or polysaccharide, mannan-oligo- and/or polysaccharide, galactomanno-oligo- and/or polysaccharides, glucomanno-oligo- and/or polysaccharides, arabinogalacto-oligo- and/or polysaccharides, fructo-oligo- and/or polysaccharides, xanthan, curdlan, laminaran, and gellan and their partially degraded derivatives.

Inclusion of SNC, particularly galactooligosaccharides, ensures a stimulation of the microflora, especially the *Bifidobacteria*, and results in fermentation products in the colon. A healthy microflora, and particularly a healthy *Bifidobacteria* count is important when infants start consuming a more mature diet, which normally comprises more pathogens than breast milk and infant nutrition. Furthermore, the bifidogenic factors as present in breast milk should be maintained in the diet in order to induce a gradual change of the intestinal flora.

The present composition preferably contains a SNC with a DP between 2 and 200, more preferably a DP between 2 and 100, more preferably a DP between 2 and 50. A lower DP of the SNC improves the fermentability by the intestinal flora and reduces viscosity of the final product. Preferably, the present composition comprises at least 5 wt. % SNC based on total fibre, more preferably at least 10 wt. %. The SNC has the additional advantage that it gives good product characteristics, e.g. the soluble fibres do not precipitate and are as good as inert towards other ingredients of the present composition.

The composition comprises preferably less than 95 wt. % SNC based on total fibre. The present composition preferably comprises 0.05 to 25 g SNC per 100 g dry weight of the composition, preferably 0.1 to 10 g, more preferably 0.5 to 5 g.

The present composition preferably comprises at least a galacto-oligosaccharide. These oligosaccharides are the same or highly similar to the galactose-based oligosaccharides present in human milk. Preferably the present composition comprises a galaco-oligosaccharides are selected from the group consisting of α-galactooligo saccharides (including raffinose and stachyose), sialylated and/or fucosylated galactooligosaccharides (including sialyllactose and fucosyllactose), lacto-N-tetraose (LNT) and lacto-N-neotetraose (neo-LNT) and β-galactooligosaccharides. Preferably the saccharides of the galacto-oligosaccharide are β-linked, as is the case in human milk. In a particularly preferred embodiment the present invention comprises the administration of transgalacto-oligosaccharide with a DP below 10. Transgalacto-oligosaccharides (TOS). These are for example sold under the trademark Vivinal™ (Borculo Domo Ingredients, Netherlands), Oligomate 55 (Yakult), CupOligo (Nissin), or Bimmuno (Clasado).

The present composition preferably comprises 0.05 to 9 g of the galacto-oligosaccharide per 100 g dry weight of the composition, more preferably 0.1 to 2 g, even more preferably 0.2 to 1 g.

Preferably, the present composition comprises a fruit-, vegetable- or cereal-based neutral, soluble, non-digestible carbohydrate, preferably a fructan. This combination makes a particularly good nutrition for the transitional period. Because fructans widely occurs in solid foods (e.g. onion, banana, artichokes) the present composition preferably comprises fructans. The term "fructans" as used herein refers to an oligosaccharide or polysaccharide comprising a chain of at least 2 β-linked fructose units, with a DP between 2 and 100, preferably between 20 and 60. Preferably inulin is used. In inulin the fructose units are linked with a β(2→1) linkage. Inulin is for instance available under the tradename "Raftilin HP®", (Orafti). Preferably the inulin has at least 90% glucose-terminated fructose chains. The average DP of the present fructan is preferably at least 9, more preferably at least 15, more preferably at least 20. The present composition preferably comprises 0.05 to 9 g of the vegetable-, fruit- and/or cereal-derived soluble non-digestible non-starch carbohydrate per 100 g dry weight of the composition, more preferably 0.1 to 2 g, even more preferably 0.2 to 1 g.

Optimally, the present nutrition comprises both the galacto-oligosaccharides (for the human milk resemblance) and the fruit-, vegetable- or cereal-based neutral, soluble, non-digestible carbohydrate (as part of the adult diet). Furthermore, an increased diversity of neutral soluble non-starch non-digestible carbohydrates stimulates a wider population of beneficial intestinal bacteria over a prolonged length of time in the colon. Preferably the weight ratio galacto-oligosaccharides: vegetable-, fruit- and/or cereal-based neutral, soluble, non-starch, non-digestible carbohydrates is 49:1 to 1:49, more preferably 19:1 to 1:19, even more preferably 9:1 to 1:9, most preferably 3:1 to 1:3.

Insoluble Non-Digestible Carbohydrates

According to a further preferred embodiment, the present composition comprises insoluble, non-digestible carbohydrates (INC). Preferably the present composition comprises between 0.1 and 7.5 g INC per 100 g dry weight, more preferably between 0.2 and 3 g, even more preferably between 0.3 and 1 g. Preferably, the present composition comprises is 5 to 95 wt. % INC based on total fibre, more preferably 10 to 50 wt. %, even more preferably 10 to 25 wt. %.

Preferably, the present composition contains resistant starch. Resistant starch is an INC that provides substrate for the colon over a prolonged period of time. Upon fermentation of resistant starch, high concentrations of butyrate are formed, which are also is found in higher concentrations in the adult colon. Butyrate has a beneficial effect on the gut barrier integrity. Hence, the butyrate content in the infant's intestine needs to be gradually increased to mature levels. Furthermore, the inclusion of resistant starch blunts blood glucose levels.

Preferably, the present composition comprises 0.01 to 5 g resistant starch per 100 g dry weight of the present composition, more preferably 0.02 to 2 g, even more preferably 0.05 to 1 g. Preferably the resistant starch is derived from cereals. The amount of resistant starch in the composition can be determined by the method described by AOAC 2002.02 and AACC 37; McCleary B V & Monaghan D A (2002) Measurement of resistant starch. *Journal of AOAC International* 85, 665-675. Preferably the resistant starch is selected from starch derived from a cereal selected from the group consisting of rice, maize and millet. A suitable source for resistant starch is HI Maize 1043 from National Starch which is derived from maize. Preferably, the present composition comprises 2 to 80 wt. % resistant starch based on total fibre, more preferably 5 to 40 wt. %, even more preferably 10 to 20 wt. %.

Preferably, the present composition further comprises insoluble non-starch polysaccharides (hereinafter abbreviated to INSP). INSP are part of the normal adult diet, but are not present in breast milk. Hence, this fibre needs to be gradually introduced in the intestinal system of the infant. INSP improve bowel habits by their water holding capacity. Preferably, the present composition comprises 0.02 to 5 g INSP per 100 g dry weight of the present composition, more preferably 0.05 to 2 g, even more preferably 0.1 to 1 g. Preferably, the present composition comprises 5 to 80 wt. % INSP based on total fibre, more preferably 10 to 40 wt. %, even more preferably 10 to 20 wt. %. Preferably the INSP is selected from the group consisting of cellulose, insoluble soy polysaccharides and hemi-cellulose. Preferably the cellulose and/or hemicellulose used in the present composition is purified from oat, rice, millet, corn, bamboo, and/or potatoes, most preferably oat. Preferably the INSC is selected from the group consisting of oat fibre, rice fibre, corn fibre, potato fibre, bamboo fibre and millet fibre, most preferably oat fibre. In one embodiment the oat fibre may alternatively be a soluble non-digestible carbohydrate.

Preferably, the present composition comprises a mixture of resistant starch and INSP, Preferably the composition comprises a mixture of resistant starch and oat fibre.

Nutrients

It is preferred a sufficient amount of digestible carbohydrates is administered to infants. Hence, preferably the digestible carbohydrates in the present composition provide 30 to 90% of the total energy content, preferably 40 to 80%. The present composition preferably comprises a combination of lactose, and digestible plant-derived carbohydrates. Lactose is the main carbohydrate source in infant milk while digestible plant carbohydrates are a main source of carbohydrates in the adult diet. The combination of lactose and digestible plant-derived carbohydrate supports the transition period.

Infants in the age of 4 to 12 months generally have their first milk teeth appearing. In order to prevent the formation of dental caries, the present composition preferably comprises less than 15 wt. % monosaccharide based on total weight of digestible carbohydrate, preferably less than 10 wt. %, most preferably less than 5 wt. %. The present composition preferably comprises between 40 and 70 wt. % disaccharide based on total weight of digestible carbohydrate, including at least 10 wt. % lactose based on total weight of digestible carbohydrate, preferably at least 40 wt. % lactose. Preferably the lactose content does not exceed 70 wt. % based on total weight of digestible carbohydrate, preferably the lactose content does not exceed 60 wt. %. In addition to lactose the present composition may e.g. include sucrose and/or maltose. Preferably a high content of lactose is included as disaccharide, since it results in attenuated blood glucose levels. Preferably digestible starch and/or maltodextrin are present. Preferably digestible starch is cereal-derived. Preferably, the digestible starch comprises slowly digestible starch. Slowly digestible starch is defined as starch which is converted to glucose between 20 and 120 minutes during in vitro digestion as described by Englyst et al. 1992. *Eur. J. Clin. Nutr.* 46 (Suppl. 2):S33-S50. The presence of slowly digestible carbohydrates has an attenuating effect on blood glucose, provides energy for a longer period of time, prolongs the feelings of satiety and reduces feeling of hunger especially during the night. Preferably the composition comprises at least 10 wt. % slowly digestible starch based on total digestible starch, more preferably at least 20 wt. %, even more preferably at least 30 wt. %. Preferably, the amount of slowly digestible starch does not exceed 70 wt. % based on total digestible starch.

Preferably the protein in the present composition provides 5 to 16% of the total energy of the present composition, more preferably 8 to 12%. Preferably the present composition comprises a protein selected from the group consisting of casein, whey, (skim) milk protein, soy protein, pea protein, collagen, rice protein, millet protein, teff protein, sorghum protein, potato protein and corn protein. The present transition nutrition preferably comprises a combination of animal protein and cereal protein. The weight ratio animal milk protein:cereal protein is preferably 1:10 to 10:1.

In still a further embodiment, the fat in the present composition preferably provides 1 to 40% of the total energy, more preferably 15 to 35%, even more preferably 20 to 30%. The amount of saturated fatty acids is preferably below 58 wt. % based on total fatty acids, more preferably below 45 wt. %. The concentration of monounsaturated fatty acids preferably ranges from 17 to 60% based on weight of total fatty acids. The concentration of polyunsaturated fatty acids in the present composition is preferably between 11 and 36% based on weight of total fatty acids. The fats are highly advantageous for the growth of the infant. The essential fatty acids linolenic acid (LA; an omega 6 fatty acid) and α-linolenic acid (ALA; an omega 3 fatty acid) preferably are present in sufficient amounts and in a balanced ratio, since LA and ALA deficiency and/or imbalance impair growth. The present composition preferably comprises 1.8 to 12.0 wt. % LA based on dry weight of the composition, and at least 0.30 wt. % ALA based on dry weight of the composition. The weight ratio LA/ALA is preferably between 5 and 15. Preferably the present composition comprises long chain polyunsaturated fatty acids (LC-PUFA), more preferably eicosapentaenoic acid (EPA) and/or docosahexaenoic acid (DHA). LC-PUFA provide a further acquaintance to ingredients in solid food, and more importantly, provide the infant with appropriate components for a good neurological development.

The present composition preferably has an increased caloric density compared to human milk and/or liquid infant formula, which is a further step towards solid nutrition. It is also important that the present composition does not have an excessive caloric density. Hence, preferably the caloric density is between 200 and 700 kcal/100 g dry weight, even more preferably between 300 and 600 kcal/100 g, most preferably between 350 and 500 kcal/100 g. In terms of caloric content, the present composition preferably comprises 5 to 16% protein; 1 to 40% fat; and 30 to 90% digestible carbohydrates based on total calories, more preferably 8 to 12% protein, 15 to 35% fat and 50 to 75% digestible carbohydrates. In other words the present composition preferably comprises comprising 5 to 16 en. % protein, 30 to 90 en. % digestible carbohydrate and 1 to 40 en. % fat, more preferably 8 to 12 en. % protein, 50 to 75 en. % digestible carbohydrate and 15 to 35 en. % fat. The term en. % is short for energy percentage and represents the relative amount each constituent contributes to the total caloric value of the composition. The present nutritional composition is particularly suitable for feeding to an infant because it provides the infant with the required nutrients.

Preferably, the composition comprises vitamins, minerals and/or trace elements. Preferably the composition comprises 3 to 10 mg iron per 100 g dry weight. The iron suitably prevent anaemia. Preferably of 1 to 3 mg zinc per 100 g dry weight of the composition. Zinc stimulates the immune system, preparing the infant for a more mature diet. The present composition preferably comprises 50 to 150 µg iodine per 100 g dry weight. This prevents iodine deficiency disorders. The present composition preferably comprises 300 to 500 mg calcium per 100 g dry weight of the composition. This improves bone health. The standard diet of infants aged 4 to 24 months is usually low in iron, iodine and zinc. Hence the present composition also solves the above problems which sometimes occur when the infant switches for breast milk to a more mature diet.

Nutritional Composition

The present composition has a viscosity of between 150 and 100,000 mPas at 20° C. and at a shear rate of 10 s$^{-1}$, preferably between 250 and 25,000 mPas, more preferably between 300 and 10,000 mPas, even more preferably between 500 and 10,000 mPas, most preferably between 1000 and 10,000 mPas. The present composition preferably has a semi-liquid and/or semi-solid constitution. Solid food is still inappropriate for infants changing from breast milk or infant liquid, because of the infant's lack of teeth and its poor swallowing reflex. Semi-liquid in the present invention refers to food products that have a viscosity above 150 mPas, but are still pourable. Semi-solid in the present invention refers to products that are still formable or spreadable but not pourable, with a viscosity up to 100,000 mPas.

Whenever the term viscosity is used in the present document, this refers to the physical parameter which is determined according to the following method: Shear flow viscosities were determined in a Paar Physika MCR 300 Modular Compact Rheometer. The instrument was equipped with a concentric cylinder geometry with a diameter of 27 mm. A logarithmic shear rate ramp is used from 0.1 to 1000 s$^{-1}$ in 20 minutes having 40 measurement points. Using the same geometry viscosities can also be measured in shear flow at a constant shear rate of 10 s$^{-1}$ for 10 minutes. The rheometer's thermostat is set on the appropriate temperature (i.e. 20° C.).

To prevent intestinal discomfort, the osmolarity of the semi-liquid and/or semi-solid nutrition of the invention is preferably between 300 and 600 mOsm/l, more preferably between 400 and 500 mOsm/l.

Preferably, the composition is in a ready-to-eat form, in which the liquid is already present. This has the advantage that the product needs only to be heated before consumption and has a stable viscosity during consumption.

The present composition is preferably present in the form of granules, flakes, puffs and/or shreds, more preferably granules.

Powder

The present composition also relates to a powder composition comprising: 10 to 99 wt. % cereal based on dry weight of the powder composition; 1.0 to 30 wt. % fibre based on dry weight of the powder composition; and 0.5 to 100 wt. % uronic acid carbohydrate with a degree of polymerisation of 10 to 300 based on total fibre.

Reconstitution of this powder with a liquid (preferably water or milk) preferably yields the present composition with a viscosity of between 150 and 100,000 mPas. Preferably 10 to 100 g powder is reconstituted with 140 ml liquid (preferably water), more preferably 14 to 80 g powder, even more preferably 30 to 65 g powder, most preferably 40 to 60 g is reconstituted with 140 ml liquid. Preferably, the liquid has a temperature of 30-70° C. upon mixing with the powder.

Hence, the present invention encompasses a packaging containing the present powder composition, wherein the packaging indicates that the powder composition is to be mixed with a suitable amount of liquid.

Preferably the powder is in an agglomerated and/or granulated form with an average particle size below 2 mm, more preferably below 1 mm.

Preferably, the composition comprises milk protein, calcium, lactose and fat. This has the advantage that the dried product can be reconstituted with water instead of milk. Water advantageously is more readily available and less prone to contamination than milk. Preferably, the fat is of vegetable origin. This has the advantage that a healthier product is obtained than when the dried product is reconstituted with cow's milk comprising more saturated fat.

Uses

The present composition is particularly useful for feeding human infants. The present composition is particularly suitable for feeding infants having the age of 4 to 36 months, more preferably having an age of 4 to 18 months, even more preferably having an age of 4 to 8 months, since that is the age by which the diet of the infant is starting to change. By administering present composition gastrointestinal discomfort, such as bloating, abdominal pain, flatulence, diarrhoea and constipation are avoided, while providing in transition both the advantages of fibres available in breast milk and the advantages of fibres for adults. The present fibre mixture comprising medium chain uronic acid carbohydrates is preferably composed in such a way that it enables a graduate change from the fibres present in breast milk to the fibres present in the mature diet. This fibre mixture is intermediate between the breast milk fibres and mature diet fibres both in quality as in quantity. The present composition can also suitably be used as clinical nutrition, for sick humans with a fragile intestinal tract. Hence in one embodiment the present composition is used in a method for providing nutrition to elderly and/or hospitalised patients.

In a preferred embodiment the composition of the invention is used prevent and/or treat diarrhoea and/or to prevent and/or treat intestinal infections. The present composition has this effect because of the beneficial effects of the fibre composition of the invention on the intestinal flora and/or the preventive effect on colon adhesion by pathogens. Preferably the present composition comprises a soluble non-digestible carbohydrate selected from the group consisting of galactooligosaccharides, fructooligosaccharides and/or fructopolysaccharides.

In a preferred embodiment the composition of the invention is used to prevent and/or treat constipation. Because of the water holding capacity and/or the effects on the intestinal flora of the fibre composition of the invention, the stool frequency is increased and/or the stools have a softer consistency, thereby preventing and/or treating constipation.

The fibre mixture of the present invention slows emptying of the stomach and slows the release of glucose into the blood and/or absorption of glucose in the small intestine. Preferably nutritional composition of the present invention comprising the fibre mixture including medium chain uronic acid carbohydrate is used to attenuate blood glucose and/or insulin levels, prolong the provision of energy, prolong the feeling of satiety, and/or improve sleep by reducing feelings of hunger. In a preferred embodiment the present invention is used to regulate blood glucose levels. In a preferred embodiment the present invention is used to reduce the post-prandial blood glucose increase. In a preferred embodiment the present invention is used to prolong the feeling of satiety. Similar terminology may be used on the packages such as reducing glycaemic index, and/or slower release of glucose into the blood.

Process

In a further aspect the present invention provides process for the manufacture of a nutritional composition, comprising admixing a) a powder comprising: 10 to 99 wt. % cereal based on dry weight of the powder; 1 to 30 wt. % based fibre based on total dry weight of the powder; and 5 to 100 wt. % uronic acid carbohydrate with a degree of polymerisation of 10 to 300 based on total fibre; and b) liquid. The mixing process preferably yields the present nutritional composition as described above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Legend FIG. 1:

Blood glucose values (mmol/1) after consumption of cereal comprising 25 g available carbohydrate with (○) or without (▲) a fibre mixture comprising oat fibre, medium chain pectin, inulin and resistant starch.

Example 1

Cereal Milk for Infants

A dry composition comprising skimmed milk powder, demineralised whey powder, vegetable fat, rice flour and ground corn, glucose, fructose, maltodextrin, fibre mixture, others (minerals, trace elements, vitamins flavours).

The composition comprises 67.9 g digestible carbohydrates per 100 g:
  13.5 g glucose
  4.7 g fructose
  21.4 g lactose
  0.5 g digestible polysaccharides (maltodextrin)
  27.6 g starch The composition comprises 2.2 g of the dietary fibre mixture per 100 g:
  2.1 wt. % medium chain pectin (from Ultra low viscosity pectin, Obipektin AG)
  47.9 wt. % inulin (from Raftiline ST, Orafti)
  8.1 wt. % resistant starch (from HI Maize 1043, National Starch)
  41.9 wt. % Oat Fibre (Vitacel Haferfaser HF 600-30, JRS)

Additionally the composition comprises 1.1 g fibre present in the cereal component. 26 g of the powder is reconstituted with 75 ml water, yielding about 100 ml. The viscosity at 20° C. and at a shear rate of 10 s$^{-1}$ at is about 8500 mPas Example 2

10 healthy adult volunteers consumed, in a cross over design, the cereal composition of example 1, reconstituted with water, comprising 25 g available, digestible carbohydrate and 1.2 g fibre (0.87 g deriving from the fibre mixture, 0.435 g fibre deriving from the cereal component) or a similar cereal composition but without the fibre mixture, reconstituted with water, comprising 25 g available, digestible carbohydrate and 0.435 g fibre deriving from the cereal. As a control 25 g glucose was consumed by the volunteers on a different day. Consumption of cereals or glucose occurred in the morning after overnight fasting. Blood glucose levels were determined at 5 minutes before consumption, at t=0, t=15, t=30, t=45, t=60, t=90 and t=120 min Results are shown in FIG. 1 and table 1.

TABLE 1

Average Incremental Area under the curve (IAUC) of Blood Glucose after Consumption of Glucose, Cereals with a Fibre Mixture or Cereals without Fibre Mixture.

| | IAUC Test product mmol/l (sd) | IAUC 25 g Glucose mmol/l (sd) | Glucose Index (GI) Value | Classification[a] |
|---|---|---|---|---|
| Control cereals N = 9* | 80 (10) | 131 (18) | 64 (5) | Medium |
| Cereals with fibre mixture N = 9* | 58 (10) | 131 (18) | 43 (5) | Low |

*1 set of data excluded as 2 s.d outside the mean
[a]Low GI <55, medium GI 55-70, high GI >70

Table 1 and FIG. 1 show that consumption of the cereal mixture comprising the fibre mixture of the present invention results in a lowered post-prandial blood glucose peak and concentration (IAUC) compared to control cereals without the fibre mixture. These results are statistically significant at t=30, t=45 and t=90 minutes. The cereal mixture of the present invention comprising the fibre mixture can be classified as a low GI food. The results are surprising since even in the presence of a high amount of glucose containing digestible carbohydrates, a relatively small amount of fibre was able to blunt blood glucose levels. These results are indicative for the beneficial effect of the present invention on regulation of blood glucose, decreasing post-prandial blood glucose levels, and/or prolonging the release of energy.

What is claimed is:

1. An infant nutritional composition with a viscosity between 150 and 100,000 mPas at 20° C. and at a shear rate of 10 s$^{-1}$, comprising:
   (a) 10 to 99 wt. % one or more cereal components based on dry weight of the nutritional composition;
   (b) 1.0 to 30 wt. % additional fiber based on dry weight of the nutritional composition, wherein the additional fiber comprises:
      (i) soluble non-digestible carbohydrates (SNC) which comprise uronic acid carbohydrates (UAC) and 10 to 95 wt. % inulin based on total fiber of the composition,
      wherein the UAC content is 0.5 to 100 wt. % UAC based on total fiber of the composition, the UAC obtained from partially degraded pectin selected from the group consisting of partially degraded apple pectin, partially degraded citrus pectin and partially degraded sugar beet pectin, and
      (ii) insoluble non-starch polysaccharides (INSP), and
   (c) minerals at the indicated concentrations per 100 gr dry weight of the composition, comprising
      (i) 3 to 10 mg iron;
      (ii) 1 to 3 mg zinc;

(iii) 300 to 500 mg calcium; and (iv) iodine consisting of 50 to 150 µg iodine.

2. The composition according to claim 1 wherein the one or more cereal components is selected from the group consisting of milled cereal, ground cereal and cereal flour.

3. The composition according to claim 1 wherein the composition comprises 5 to 95 wt. % SNC based on total fiber,
wherein the SNC further comprise one or more other SNC selected from the group consisting of galacto-oligosaccharides, galacto-polysaccharides, xylo-oligsaccharides, xylo-polysaccharides, gluco-oligosaccharides, gluco-polysaccharides, malto-oligosaccharides, isomalto-oligosaccharides, resistant dextrins, cyclodextrins, arabino-oligosaccharides, mannan-oligosaccharides, galactomanno-oligosaccharides, galactomanno-polysaccharides, glucomanno-oligosaccharides, glucomanno-polysaccharides, arabinogalacto-oligosaccharides, arabinogalacto-polysaccharides fructo-oligosaccharides, and fructopolysaccharides.

4. The composition according to claim 1 wherein the additional fiber further comprises resistant starch.

5. The composition according to claim 4 wherein:
(a) the concentration of the one or more cereal components is 20 to 90 wt. % based on dry weight of the composition;
(b) said one or more cereal components are cereal flour, milled cereals and/or ground cereals;
(c) the concentration of the additional fiber is 1.5 to 20 wt. % based on dry weight of the composition, wherein
(i) the UAC content is 0.5 to 86 wt. % UAC based on total fiber and the UAC has a degree of polymerization of 10 to 300;
(ii) the resistant starch is in an amount of 2 to 80 wt. % based on total fiber; and
(iii) the INSP comprises 2 to 80 wt. % oat fiber based on total fiber.

6. The composition according to claim 1 wherein said one or more cereal components is selected from the group consisting of millet flour, rice flour, corn flour, teff flour, oat flour, sorghum flour and starchy root crops flour.

7. The composition according to claim 1 further comprising 10 to 70 wt. % slowly digestible starch based on total digestible starch.

8. The composition according to claim 1 wherein the composition comprises 5 to 16 en. % protein, 30 to 90 en. % digestible carbohydrate and 1 to 40 en. % fat.

9. A powder composition for feeding infants comprising:
(a) 10 to 99 wt. % cereal flour, milled cereals and/or ground cereals based on dry weight of the powder composition;
(b) 1.0 to 30 wt. % additional fiber based on dry weight of the powder composition, and wherein the additional fiber comprises:
(i) soluble non-digestible carbohydrate (SNC) which comprise uronic acid carbohydrates (UAC),
wherein the UAC content of the powder composition is 0.5 to 100 wt. % UAC based on total fiber, the UAC obtained from partially degraded pectin selected from the group consisting of partially degraded apple pectin, partially degraded citrus pectin and partially degraded sugar beet pectin, and
(ii) insoluble non-starch polysaccharides (INSP); and
(c) minerals at the indicated concentrations per 100 gr dry weight of the powder composition, comprising
(i) 3 to 10 mg iron;
(ii) 1 to 3 mg zinc;
(iii) 300 to 500 mg calcium; and (iv) iodine consisting of 50 to 150 µg iodine.

10. The powder composition according to claim 9 wherein the composition comprises:
(a) 20 to 90 wt. % cereal flour, milled cereal and/or ground cereal based on dry weight of the powder composition; and
(b) 1.5 to 20 wt. % additional fiber based on dry weight of the powder composition, wherein:
(i) the UAC content of the powder composition is 0.5 to 86 wt. % UAC based on total fiber,
(ii) the SNC further comprises 10 to 95 wt. % insulin based on total fiber,
(iii) the INSP comprises 2 to 80 wt. % oat fiber based on total fiber, and
(iv) the powder composition further comprises 2 to 80 wt. % resistant starch based on total fiber.

11. The composition according to claim 5 wherein the degree of polymerization of the UAC is 20-200.

12. The powder composition according to claim 9 wherein the UAC has a degree of polymerization of 10 to 300.

13. The powder composition according to claim 12 wherein the UAC has a degree of polymerization of 20 to 200.

14. The composition according to claim 1 wherein the osmolarity of the nutritional composition is between 300 and 600 mOsm/l.

15. The composition according to claim 14 wherein the osmolarity of the nutritional composition is between 400 and 500 mOsm/l.

* * * * *